United States Patent [19]

Purewal et al.

[11] Patent Number: 5,225,183
[45] Date of Patent: Jul. 6, 1993

[54] MEDICINAL AEROSOL FORMULATIONS

[75] Inventors: Tarlochan S. Purewal, Leamington Spa; David J. Greenleaf, Loughborough, both of England

[73] Assignee: Riker Laboratories, Inc., St. Paul, Minn.

[21] Appl. No.: 649,140

[22] Filed: Jan. 30, 1991

Related U.S. Application Data

[63] Continuation of Ser. No. 442,119, Nov. 28, 1989, abandoned.

[30] Foreign Application Priority Data

Dec. 6, 1988 [GB] United Kingdom ............... 8828477

[51] Int. Cl.$^5$ .............................................. A61L 9/04
[52] U.S. Cl. ..................................... 424/45; 424/46; 424/451; 514/180; 514/183
[58] Field of Search .................... 424/45, 46, 451; 514/180, 183

[56] References Cited

U.S. PATENT DOCUMENTS

| | | | |
|---|---|---|---|
| 2,868,691 | 1/1959 | Porush et al. | 167/54 |
| 3,014,844 | 12/1961 | Thiel et al. | 167/82 |
| 4,161,516 | 7/1979 | Bell | 424/451 |
| 4,174,295 | 11/1979 | Bargigia et al. | 252/305 |
| 4,405,598 | 9/1983 | Brown | 424/45 |
| 4,428,854 | 1/1984 | Enjo et al. | 252/69 |
| 4,590,206 | 5/1986 | Forrester et al. | 514/456 |
| 4,601,897 | 7/1986 | Saxton | 424/45 |
| 4,814,161 | 3/1989 | Jinks et al. | 514/506 |
| 4,866,051 | 9/1989 | Hunt et al. | 514/180 |

FOREIGN PATENT DOCUMENTS 2737132 2/1978 Fed. Rep. of Germany .
2046093 11/1980 United Kingdom .

OTHER PUBLICATIONS

Research Disclosure, vol. 162, 1977, p. 70 (#16265)
Search Report of corresponding EPO application.
International Journal of Refrigeration 1988, 11, 389 (Spauschus, Nov. 1988).
"Manufacturing Chemist", Feb. 1988, p. 9.
"Processing", Dec. 1988, p. 7.
"Fluorocarbons and Ozone" Apr. 1988.
Manufacturing Chemist, Sep. 1988, p. 9.
Manufacturing Chemist, Jun. 1988, p. 3.
Aerosol Age, Jul. 1988, pp. 28-31.
New Scientist, May 26, 1988, pp. 56-60.
Western Union "Mailgram", DuPont, Mar. 24, 1988.
Aerosol Age, Aug. 1988, pp. 32-39.

*Primary Examiner*—Thurman K. Page
*Assistant Examiner*—William E. Benston, Jr.
*Attorney, Agent, or Firm*—Gary L. Griswold; Walter N. Kirn; Douglas E. Reedich

[57] ABSTRACT

A self-propelling aerosol formulation which may be free from CFC's which comprises a medicament, 1,1,1,2-tetrafluoroethane, a surface active agent and at least one compound having a higher polarity than 1,1,1,2-tetrafluoroethane.

3 Claims, No Drawings

MEDICINAL AEROSOL FORMULATIONS

This is a continuation of application Ser. No. 07/442,119 filed Nov. 28, 19989, now abandoned.

FIELD OF THE INVENTION

This invention relates to medicinal aerosol formulations and in particular to formulations suitable for pulmonary, nasal, buccal or topical administration which are at least substantially free of chlorofluorocarbons.

BACKGROUND TO THE INVENTION

Since the metered dose pressurised inhaler was introduced in the mid 1950's, inhalation has become the most widely used route for delivering bronchodilator drugs and steroids to the airways of asthmatic patients. Compared with oral administration of bronchodilators, inhalation offers a rapid onset of action and a low instance of systemic side effects. More recently, inhalation from a pressurised inhaler has been a route selected for the administration of other drugs, e.g., ergotamine, which are not primarily concerned with treatment of a bronchial malady.

The metered dose inhaler is dependent upon the propulsive force of a propellant system used in its manufacture. The propellant generally comprises a mixture of liquified chlorofluorocarbons (CFC's) which are selected to provide the desired vapour pressure and stability of the formulation. Propellants 11, 12 and 114 are the most widely used propellants in aerosol formulations for inhalation administration.

In recent years it has been established that CFC's react with the ozone layer around the earth and contribute towards its depletion. There has been considerable pressure around the world to reduce substantially the use of CFC's, and various Governments have banned the "non-essential" use of CFC's. Such "non-essential" uses include the use of CFC's as refrigerants and blowing agents, but heretofore the use of CFC's in medicines, which contributes to less than 1% of the total use of CFC's, has not been restricted. Nevertheless, in view of the adverse effect of CFC's on the ozone layer it is desirable to seek alternative propellant systems which are suitable for use in inhalation aerosols.

U.S. patent specification No. 4,174,295 discloses aerosol propellant compositions which consist of a mixture of a hydrogen-containing chlorofluorocarbon or fluorocarbon (A), selected from the group consisting of $CHClF_2$ (Freon 22), $CH_2F_2$ (Freon 32) and $CF_3-CH_3$ (Freon 143a), with a hydrogen-containing fluorocarbon or chlorofluorocarbon (B) selected from the group consisting of: $CH_2ClF$ (Freon 31), $CClF_2-CHClF$ (Freon 123a), $CF_3-CHCl$ (Freon 124), $CHF_2-CClF_2$ (Freon 124a), $CHClF-CHF_2$ (Freon 133), $CF_3-CH_2Cl$ (Freon 133a), $CHF_2-CHF_2$ (Freon 134), $CF_3-CH_2F$ (Freon 134a), $CClF_2-CH_3$ (Freon 142b) and $CHF_2-CH_3$ (Freon 152a). The compositions may contain a third component (C) consisting of a saturated hydrocarbon propellant, e.g., n-butane, isobutane, pentane and isopentanes. The propellant compositions comprise 5 to 60% of (A), 5 to 95% of (B) and 0 to 50% of (C) and are said to be suitable for application in the fields of: hair lacquers, anti-perspiration products, perfumes, deodorants for rooms, paints, insecticides, for home cleaning products, for waxes, etc. The compositions may contain dispersing agents and solvents, e.g., methylene chloride, ethanol etc.

It has now been found that 1,1,1,2-tetrafluoroethane has particularly suitable properties for use as a propellant for medicinal aerosol formulations when used in combination with a surface active agent and an adjuvant having a higher polarity than 1,1,1,2-tetrafluoroethane.

SUMMARY OF THE INVENTION

According to the present invention there is provided an aerosol formulation comprising a medicament, a surfactant, 1,1,1,2-tetrafluoroethane and at least one compound having a higher polarity than 1,1,1,2-tetrafluoroethane.

It has been found that 1,1,1,2-tetrafluoroethane, hereinafter referred to as Propellant 134a, may be employed as a propellant for aerosol formulations suitable for inhalation therapy when used in combination with a compound (hereinafter an "adjuvant") having a higher polarity than Propellant 134a. The adjuvant should be miscible with Propellant 134a in the amounts employed. Suitable adjuvants include alcohols such as ethyl alcohol, isopropyl alcohol, propylene glycol, hydrocarbons such as propane, butane, isobutane, pentane, isopentane, neopentane, and other propellants such as those commonly referred to as Propellants 11, 12, 114, 113, 142b, 152a 124, and dimethyl ether. The combination of one or more of such adjuvants with Propellant 134a provides a propellant system which has comparable properties to those of propellant systems based on CFC's, allowing use of known surfactants and additives in the pharmaceutical formulations and conventional valve components. This is particularly advantageous since the toxicity and use of such compounds in metered dose inhalers for drug delivery to the human lung is well established. Preferred adjuvants are liquids or gases at room temperature (22° C.) at atmospheric pressure.

Recently it has been established that certain CFC's which have been used as anaesthetics are not significantly ozone depleting agents as they are broken down in the lower atmosphere. Such compounds have a higher polarity than Propellant 134a and may be employed in the composition of the invention. Examples of such compounds include 2-bromo-2-chloro-1,1,1,-trifluoroethane, 2-chloro-1-(difluoromethoxy)-1,1,2-trifluroethane and 2-chloro-2-(difluromethoxy)-1,1-trifluoroethane.

In contrast to the prior art the compositions of the invention do not require the presence of Freon 22, Freon 32 or Freon 143a to provide useful properties; these propellants are preferably absent or present in minor amounts of less than 5% by weight of the propellant composition. The compositions are preferably free from CFC's.

The particular adjuvant(s) used and the concentration of the adjuvant(s) is selected according to the particular medicament used and the desired physical properties of the formulation.

It has been found that the use of Propellant 134a and drug as a binary mixture or in combination with a conventional surfactant such as sorbitan trioleate does not provide formulations having suitable properties for use with pressurised inhalers. It has been established lo that the physical parameters of polarity, vapour pressure, density, viscosity and interfacial tension are all important in obtaining a stable aerosol formulation, and by a suitable selection of a compound having a polarity higher than that of Propellant 134a stable aerosol formulations using Propellant 134a may be prepared.

The addition of a compound of higher polarity than Propellant 134a to Propellant 134a provides a mixture in which increased amounts of surfactant may be dissolved compared to their solubility in Propellant 134a alone. The presence of increased amounts of solubilised surfactant allows the preparation of stable, homogenous suspensions of drug particles. The presence of large amounts of solubilised surfactant may also assist in obtaining stable solution formulations of certain drugs.

The polarity of Propellant 134a and of an adjuvant may be quantified, and thus compared, in terms of a dielectric constant, or by using Maxwell's equation to relate dielectric constant to the square of the refractive index—the refractive index of materials being readily measurable or obtainable from the literature.

Alternatively, the polarity of adjuvants may be measured using the Kauri-butanol value for estimation of solvent power. The protocol is described in ASTM Standard: Designation 1133-86. However, the scope of the aforementioned test method is limited to hydrocarbon solvents having a boiling point over 40° C. The method has been modified as described below for application to more volatile substances such as is required for propellant.

Standardisation

In conventional testing the Kauri resin solution is standardised against toluene, which has an assigned value of 105, and a mixture of 75% n-heptane and 25% toluene by volume which has an assigned value of 40. When the sample has a Kauri-butanol value lower than 40, it is more appropriate to use a single reference standard of 75% n-heptane: 25% toluene. The concentration of Kauri-butanol solution is adjusted until a titer between 35ml and 45ml of the reference standard is obtained using the method of the ASTM standard.

Method for Volatile Compounds

The density of the volatile substance under test is calculated to allow a volumetric titration from the added weight of the sample after testing.

Kauri-butanol solution (20g) is weighed into an aerosol bottle. A non-metering value is crimped onto the bottle and the weight of bottle and sample measured. Following the procedure detailed in ASTM standards as closely as possible, successive amounts of the volatile sample are transferred from an aerosol bottle via a transfer button until the end point is reached (as defined in ASTM). The aerosol bottle with titrated Kauri-butanol solution is re-weighed.

The Kauri-butanol value is calculated using the following formula:

$$V = \frac{(W_2 - W_1)}{d} \times \frac{40}{B}$$

in which:
$W_2$ = weight of aerosol bottle after titration (g)
$W_1$ = weight of aerosol bottle before titration (g)
d = density of sample (g/ml)

B is as defined in the ASTM standard and = ml of heptane-toluene blend required to titrate 20g of Kauri-butanol solution.

If a titer (V) is obtained by precipitation of the Kauri resin out of solution, then a higher Kauri-butanol value represents a sample of higher polarity.

If the sample and Kauri-butanol solution are immiscible, this is most likely to be due to the immiscibility of the sample with butanol resulting from an excessively low polarity. However, it is feasible that excessively high polarity could result in immiscibility. This is tested by checking the miscibility of the sample with water. If the sample is immiscible with water and immiscible with Kauri-butanol solution, then the Kauri-butanol value is deemed too low to be measured, and the polarity is to be regarded as lower than that of any material which would give a proper titer into Kauri-butanol solution.

The particular selection of adjuvant and concentration preferably provides the resulting mixture with a solubility parameter of from 6.0 to 8.5 $(cal/cm^3)^{\frac{1}{2}}$. A propellant system having a solubility parameter below 6.0 $(cal/cm^3)^{\frac{1}{2}}$ is a pooor solvent for surfactants, resulting in unstable suspension formulations of drug. The preferred solubility parameter for the propellant system comprising Propellant 134a and adjuvant is in the range 6.5 to 7.8 $(cal/cm^3)^{\frac{1}{2}}$.

The vapour pressure of a propellant system is an important factor as it provides the propulsive force for the medicament. The adjuvant is selected to moderate the vapour pressure of Propellant 134a so that it is within the desired range. This allows for advantages in the manufacture of the dosage form and gives greater flexibility to obtain and vary the target vapour pressure at room temperature. Another factor in the choice of the adjuvant is that, whilst it should allow moderation of the vapour pressure of Propellant 134a, it should not easily demix when the mixture is cooled to lower temperatures for the purposes of manufacture of the aerosol formulation and filling the containers.

The vapour pressure may also be increased if desired depending on the choice of the adjuvant. It has been found that some of the propellant mixtures deviate from Raoult's Law. The addition of certain alcohols makes very little change to the vapour pressure of the mixture with Propellant 134a at room temperature. However addition of certain hydrocarbons having a lower vapour pressure than Propellant 134a can result in a mixture having a higher vapour pressure.

The vapour pressure of the formulations at 25° C. is generally in the range 20 to 150 psig (1.4 to $1.3 \times 10^5$ $N/m^2$) preferably in the range 40 to 90 psig (2.8 to $6.2 \times 10^5$ $N/m^2$).

The selection of adjuvant may also be used to modify the density of the formulation. Suitable control of the density may reduce the propensity for either sedimentation or "creaming" of the dispersed drug powders. The density of the formulations is generally in the range 0.5 to 2.0 $g/cm^3$, preferably in the range 0.8 to 1.8 $g/cm^3$, more preferably in the range 1.0 to 1.5 $g/cm^3$.

The selection of adjuvant may also be used to adjust the viscosity of the formulation which is desirably less than 10 cP.

The selection of adjuvant may also be used to adjust the interfacial tension of the propellant system. In order to optimise dispersion of drug particles and stability the interfacial tension of the formulation is desirably below 70 dynes/cm.

Propellant 134a is generally present in the aerosol formulations in an amount of at least 50% by weight of the formulation, normally 60 to 95% by weight of the formulation.

Propellant 134a and the component of higher polarity are generally employed in the weight ratio 50:50 to 99:1 Propellant 134a : high polarity component, preferably in the weight ratio 70:30 to 98:2 and more preferably in the weight ratio 85:15 to 95:5 Propellant 134a : high polarity component. Preferred compounds of higher polarity than Propellant 134a include ethanol, pentane, isopentane and neopentane.

The aerosol formulations comprise a surface active agent to stabilise the formulation and lubricate the valve components. Suitable surface active agents include both non-fluorinated surfactants and fluorinated surfactants known in the art and disclosed, for example, in British Patent Nos. 837465 and 994734 and U.S. Pat. No. 4,352,789. Examples of suitable surfactants include: oils derived from natural sources, such as, corn oil, olive oil, cotton seed oil and sunflower seed oil.

Sorbitan trioleate available under the trade name Span 85,

Sorbitan mono-oleate available under the trade name Span 80,

Sorbitan monolaurate available under the trade name Span 20,

Polyoxyethylene (20) sorbitan monolaurate available under the trade name Tween 20, Polyoxyethylene (20) sorbitan mono-oleate available under the trade name Tween 80, lecithins derived from natural sources such as those available under the trade name Epikuron particularly Epikuron 200.

Oleyl polyoxyethylene (2) ether available under the trade name Brij 92,

Stearyl polyoxyethylene (2) available under the trade name Brij 72,

Lauryl polyoxyethylene (4) ether available under the trade name Brij 30,

Oleyl polyoxyethylene (2) ether available under the trade name Genapol 0-020,

Block copolymers of oxyethylene and oxypropylene available under the trade name Synperonic, Oleic acid, Synthetic lecithin, Diethylene glycol dioleate, Tetrahydrofurfuryl oleate, Ethyl oleate, Isopropyl myristate, Glyceryl trioleate, Glyceryl monolaurate, Glyceryl mono-oleate, Glyceryl monostearate, Glyceryl monoricinoleate, Cetyl alcohol, Stearyl alcohol, Polyethylene glycol 400, Cetyl pyridinium chloride.

The surface active agents are generally present in amounts not exceeding 5 percent by weight of the total formulation. They will usually be present in the weight ratio 1:100 to 10:1 surface active agent: drug(s), but the surface active agent may exceed this weight ratio in cases where the drug concentration in the formulation is very low.

Suitable solid medicaments include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, and synergistic combinations of these. Examples of medicaments which may be employed are: Isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine. Others are antibiotics, such as neomycin, streptomycin, penicillin, procaine penicillin, tetracycline, chlorotetracycline and hydroxytetracycline; adrenocorticotropic hormone and adrenocortical hormones, such as cortisone, hydrocortisone, hydrocortisone acetate and prednisolone; insulin, antiallergy compounds such as cromolyn sodium, etc.

The drugs exemplified above may be used as either the free base or as one or more salts known to the art. The choice of free base or salt will be influenced by the physical stability of the drug in the formulation. For example, it has been shown that the free base of salbutamol exhibits a greater dispersion stability than salbutamol sulphate in the formulations of the invention.

The following salts of the drugs mentioned above may be used; acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphatediphosphate, polygalacturonate, salicylate, stearate, subacetate, succinate, sulphate, tannate, tartrate, and triethiodide.

Cationic salts may also be used. Suitable cationic salts include the alkali metals, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol-amino-2-(hydroxymethyl)propane-1,3-diol and 1-(3,4-dihydroxyphenyl)-2 isopropylaminoethanol.

For pharmaceutical purposes the particle size of the powder should desirably be no greater than 100 microns diameter, since larger particles may clog the valve or orifice of the container. Preferably the particle size should be less than 25 microns in diameter. Desirably the particle size of the finely-divided solid powder should for physiological reasons be less than 25 microns and preferably less than about 10 microns in diameter. The particle size of the powder for inhalation therapy should preferably be in the range 2 to 10 microns.

There is no lower limit on particle size except that imposed by the use to which the aerosol produced is to be put. Where the powder is a solid medicament, the lower limit of particle size is that which will be readily absorbed and retained on or in body tissues. When particles of less than about one-half micron in diameter are administered by inhalation they tend to be exhaled by the patient.

The concentration of medicament depends upon the desired dosage but is generally in the range 0.01 to 5% by weight.

The formulation of the invention may be filled into conventional aerosol containers equipped with metering valves and dispensed in an identical manner to formulations employing CFC's.

The invention will now be illustrated by the following Examples.

The following components were used in the Examples:

| | |
|---|---|
| Salbutamol Sulphate B.P., micronised | Salbutamol |
| Beclomethasone Dipropionate Isopropylacohol solvate, micronised | BDP |

-continued

| | |
|---|---|
| Sodium Cromoglycate B.P., micronised | DSCG |
| Sorbitan trioleate | Span 85 |
| Lecithin commercially available under the trade name Lipoid S100 | Lipoid S100 |
| Oleic Acid B.P. | oleic acid |
| 1,1,1,2-Tetrafluoroethane | P134a |
| Ethyl alcohol B.P. | ethanol |
| n-Pentane, standard laboratory reagent | n-pentane |

The formulations in the Examples were prepared by the following techniques.

Each drug and surfactant combination was weighed into a small beaker. The required quantity of the higher boiling point component of the propellant system e.g. ethanol was added and the mixture homogenised using a Silverson mixer. The required quantity of the mixture was dispensed into a P.E.T. bottle and an aerosol valve crimped in place. Propellant 134a was added to the required weight by pressure filling.

EXAMPLES 1 TO 6

Formulations containing Salbutamol

The formulations reported in the following Tables were prepared.

| | Example No. | | | | | |
|---|---|---|---|---|---|---|
| Ingredient (g) | 1 | 2 | 3 | 4 | 5 | 6 |
| Salbutamol | 0.010 | 0.010 | 0.010 | 0.010 | 0.010 | 0.010 |
| Span 85 | 0.012 | — | — | 0.012 | — | — |
| Oleic Acid | — | 0.012 | — | — | 0.012 | — |
| Lipoid S100 | — | — | 0.012 | — | — | 0.012 |
| n-Pentane | 1.240 | 1.240 | 1.240 | — | — | — |
| Ethanol | — | — | — | 1.350 | 1.350 | 1.350 |
| P134a | 3.720 | 3.720 | 3.720 | 4.040 | 4.040 | 4.040 |

All formulations comprised a suspension of salbutamol. Examples 4 to 6 containing ethanol appeared to be more stable than Examples 1 to 3 containing n-pentane, exhibiting a decreased tendency to settling.

EXAMPLES 7 TO 12

Formulations containing Beclomethasone Dipropionate

The formulations reported in the following Tables were prepared.

| | Example No. | | | | | |
|---|---|---|---|---|---|---|
| Ingredient (g) | 7 | 8 | 9 | 10 | 11 | 12 |
| BDP | 0.005 | 0.005 | 0.005 | 0.005 | 0.005 | 0.005 |
| Span 85 | 0.012 | — | — | 0.006 | — | — |
| Oleic Acid | — | 0.012 | — | — | 0.006 | — |
| Lipoid S100 | — | — | 0.006 | — | — | 0.006 |
| n-Pentane | 1.240 | 1.240 | 1.240 | — | — | — |
| Ethanol | — | — | — | 1.350 | 1.350 | 1.350 |
| P134a | 3.720 | 3.720 | 3.720 | 4.040 | 4.040 | 4.040 |

For those formulations containing n-pentane, Examples 7 and 8 appeared less turbid than Example 9, and Example 8 appeared to form a solution after 4-5 days.

Examples 10 to 12 produced solution formulations.

EXAMPLES 13 to 18

Formulations containing Sodium Cromoglycate

The formulations reported in the following Tables were prepared.

| | Example No. | | | | | |
|---|---|---|---|---|---|---|
| Ingredient (g) | 13 | 14 | 15 | 16 | 17 | 18 |
| DSCG | 0.100 | 0.100 | 0.100 | 0.100 | 0.100 | 0.100 |
| Span 85 | 0.024 | — | — | 0.006 | — | — |
| Oleic Acid | — | 0.024 | — | — | 0.006 | — |
| Lipoid S100 | — | — | 0.024 | — | — | 0.006 |
| n-Pentane | 1.240 | 1.240 | 1.240 | — | — | — |
| Ethanol | — | — | — | 1.350 | 1.350 | 1.350 |
| P134a | 3.720 | 3.720 | 3.720 | 4.040 | 4.040 | 4.040 |

Examples 13 to 18 produced suspension formulations, Examples 16 to 18 containing ethanol exhibiting better stability properties than Examples 13 to 15 containing n-pentane.

EXAMPLES 19 to 23

The following Examples illustrate the use of different adjuvants with Propellant 134a.

| | Example No. | | | | |
|---|---|---|---|---|---|
| Ingredient (g) | 19 | 20 | 21 | 22 | 23 |
| Salbutamol | 0.012 | 0.012 | 0.012 | 0.012 | — |
| BDP | — | — | — | — | 0.010 |
| Span 85 | 0.001 | 0.001 | 0.001 | 0.001 | — |
| Oleic Acid | — | — | — | — | 0.001 |
| P134a | 4.98 | 5.22 | 5.28 | 5.61 | 5.04 |
| neopentane | 0.55 | — | — | — | — |
| Isopropyl-alcohol | — | 0.58 | — | — | — |
| Isopropyl-myristate | — | — | 0.59 | — | — |
| Propellant 11 | — | — | — | 0.62 | — |
| Isopentane | — | — | — | — | 0.56 |

Each Example was 5 ml in volume and was in the form of a stable suspension.

EXAMPLE 24

This Example illustrates the use of different surfactants in the following basic formulations:

| | |
|---|---|
| Salbutamol | 0.012 g |
| Ethanol | 0.58 g |
| P134a | 5.220 g |
| Surfactant | A or B |

Volume = 5 ml
A = 0.005 g
B = 0.012 g

The following surfactants were employed to form stable suspensions in the concentrations specified.

| | |
|---|---|
| 1. Span 85 | A, B. |
| 2. Span 80 | A. |
| 3. Span 20 | A. |
| 4. Tween 20 | A. |
| 5. Tween 80 | A. |
| 6. Oleic acid | A, B. |
| 7. Epikuron 200 | B. |
| 8. Synthetic lecithin | B. |
| 9. Brij 92 | A. |
| 10. Brij 72 | A. |
| 11. Brij 30 | B. |
| 12. Genapol 0-020 | A. |
| 13. Diethylene glycol dioleate | A. |
| 14. Tetrahydrofurfuryl oleate | A. |
| 15. Ethyl oleate | A. |
| 16. Isopropyl myristate | B. |
| 17. Glyceryl trioleate | A, B. |
| 18. Glyceryl monolaurate | A. |
| 19. Glyceryl mono-oleate | A. |

-continued

| | | |
|---|---|---|
| 20. Glyceryl monostearate | A. | |
| 21. Glyceryl monoricinoleate | A. | |
| 22. Cetyl alcohol | A. | |
| 23. Stearyl alcohol | B. | |
| 24. Polyethylene glycol 400 | B. | |
| 25. Synperonic PE L61 | A. | |
| 26. Synperonic PE L64 | A. | |
| 27. Synperonic PE L92 | A. | |
| 28. Synperonic PE P94 | A. | |
| 29. Cetyl pyridinium chloride | A. | |
| 30. FC 807 free acids (consisting mainly of bis(perfluoro-n-octyl-N-ethyl sulphonamidoethyl) phosphate) | A, B. | |
| 31. Corn Oil | B. | |

We claim:

1. An aerosol formulation comprising:
   (a) a therapeutically effective amount of a medicament;
   (b) a propellant substantially free of chlorofluorocarbons, said propellant comprising 1,1,1,2-tetrafluoroethane;
   (c) a surface active agent in an amount sufficient (i) to stabilize the formulation or (ii) lubricate a valve stem in a metering valve; and
   (d) at least one compound selected from the group consisting of ethyl alcohol, isopropyl alcohol, n-pentane, isopentane, neopentane, isopropyl, and myristate, said compound being present in an amount such that it is miscible with the 1,1,1,2-tetrafluoroethane and such that said surface active agent is soluble in the formulation in a greater amount than in 1,1,1,2-tetrafluoroethane.

2. The formulation of claim 1 wherein the weight ratio of 1,1,1,2-tetrafluoroethane to compound (d) is in the range of 50:50 to 99:1.

3. The formulation of claim 1 wherein said medicament is a member selected from the group consisting of salbutamol, beclomethasone dipropionate, disodium cromoglycate, pirbuterol, isoprenaline, adrenaline, rimiterol, and ipratropium bromide.

* * * * *

UNITED STATES PATENT AND TRADEMARK OFFICE
CERTIFICATE OF CORRECTION

PATENT NO. : 5,225,183
DATED : July 6, 1993
INVENTOR(S) : Tarlochan S. Purewal et al.

It is certified that error appears in the above-identified patent and that said Letters Patent is hereby corrected as shown below:

Col. 1, 5, "19989" should read --1989--.
Col. 1, line 54, "CF$_3$-CHCl" should read --CF$_3$-CHClF--.
Col. 2, line 45-46, "-1,1-trifluoroethane" should read ---1,1,1-trifluoroethane--.
Col. 2, line 62, delete "lo".
Col. 4, line 44, "1.3" should read --10.3--.
Col. 6, lines 23-24, "phosphatediphosphate" should read --phosphate/diphosphate--.

Signed and Sealed this

Fourteenth Day of June, 1994

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO.: 5,225,183

DATED: July 6, 1993

INVENTOR(S): Tarlocan S. Purewal et al.

It is certified that error appears in the above-identified patent and that said Letters Patent is hereby corrected as shown below:

Col. 10, lines 9-10, "isopropyl, and myristate," should read --isopropyl myristate,--.

Signed and Sealed this

Eleventh Day of March, 1997

Attest:

BRUCE LEHMAN

Attesting Officer

Commissioner of Patents and Trademarks